(12) United States Patent
Noland et al.

(10) Patent No.: US 11,080,361 B2
(45) Date of Patent: Aug. 3, 2021

(54) INTEGRATED REMOTE SENSING TOOLS FOR TIMELY PREDICTIONS OF CROP QUALITY AND YIELD

(71) Applicant: Regents of the University of Minnesota, Minneapolis, MN (US)

(72) Inventors: Reagan Noland, Minneapolis, MN (US); Scott Wells, Minneapolis, MN (US); Craig Sheaffer, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 727 days.

(21) Appl. No.: 15/663,112

(22) Filed: Jul. 28, 2017

(65) Prior Publication Data

US 2018/0039600 A1     Feb. 8, 2018

Related U.S. Application Data

(60) Provisional application No. 62/371,294, filed on Aug. 5, 2016.

(51) Int. Cl.
| | |
|---|---|
| *G06F 17/11* | (2006.01) |
| *A01B 79/00* | (2006.01) |
| *G01J 1/42* | (2006.01) |
| *G01N 33/02* | (2006.01) |
| *B64C 39/02* | (2006.01) |
| *B64D 47/08* | (2006.01) |

(52) U.S. Cl.
CPC ............ *G06F 17/11* (2013.01); *A01B 79/005* (2013.01); *B64C 39/024* (2013.01); *B64D 47/08* (2013.01); *G01J 1/4204* (2013.01); *G01N 33/025* (2013.01); *B64C 2201/12* (2013.01); *B64C 2201/127* (2013.01); *G01J 2001/4266* (2013.01)

(58) Field of Classification Search
CPC ..... G06F 17/11; A01B 79/005; B64C 39/024; B64C 2201/12; B64C 2201/127; B64D 47/08; G01J 1/4204; G01J 2001/4266; G01N 33/025
USPC .......................................................... 703/2
See application file for complete search history.

(56) References Cited

U.S. PATENT DOCUMENTS

| | | | |
|---|---|---|---|
| 6,967,656 B2* | 11/2005 | Black .................. | A01B 79/005 345/440 |
| 2004/0032973 A1* | 2/2004 | Robeson .............. | A01B 79/005 382/110 |

(Continued)

OTHER PUBLICATIONS

Jay, Sylvain, et al. "In-field crop row phenotyping from 3D modeling performed using Structure from Motion." Computers and Electronics in Agriculture 110 (2015): 70-77.*

(Continued)

*Primary Examiner* — Justin C Mikowski
(74) *Attorney, Agent, or Firm* — Theodore M. Magee; Westman, Champlin & Koehler, P.A.

(57) ABSTRACT

A method includes receiving outside temperatures for a plurality of days and calculating growing degree units based on the received temperatures. Intensities for a plurality of wavelengths of light measured over at least one portion of a field containing a crop are received and are used with the growing degree units to predict a quality value for the crop. The predicted quality value for the crop is then displayed.

16 Claims, 5 Drawing Sheets

(56) References Cited

U.S. PATENT DOCUMENTS

| | | | |
|---|---|---|---|
| 2009/0106163 A1* | 4/2009 | Foresman | G06Q 30/00 705/80 |
| 2014/0222374 A1* | 8/2014 | Lock | A01B 79/005 702/166 |
| 2015/0073716 A1* | 3/2015 | Johnson | G06Q 50/02 702/19 |
| 2016/0084813 A1* | 3/2016 | Anderson | A01D 41/127 702/5 |
| 2016/0183547 A1* | 6/2016 | Lawrence | A23B 9/00 426/231 |
| 2017/0089742 A1* | 3/2017 | Bruns | A01D 41/1273 |

OTHER PUBLICATIONS

Singh, K. K., et al. "Performance evaluation of medium-range weather forecast using crop growth simulator." Journal of Environmental Systems 25 (1997): 397-408.*

Albayrak, Use of reflectance measurements for the detection of N, P, K, ADF and NDF contents in sainfoin pasture, Sensors, vol. 8, pp. 7275-7286, 2008.

Berni et al., Mapping canopy conductance and CWSI in olive orchards using high resolution thermal remote sensing imagery, Remote Sens. Environ. vol. 113, pp. 2380-2388, 2009.

Bourgeois et al., Evaluation of an alfalfa growth simulation model under Quebec conditions, Agricultural Systems, vol. 32, pp. 1-12, 1990.

Bouton, The economic benefits of forage improvement in the United States, Euphytica, vol. 154, pp. 263-270, 2007.

Buxton, Quality-related characteristics of forages as influenced by plant environment and agronomic factors, Animal Feed Science Technology, vol. 59, pp. 37-49, 1996.

Confalonieri et al., A preliminary evaluation of the simulation model CropSyst for alfalfa, European Journal of Agronomy, vol. 21, pp. 223-237, 2004.

Daughtry, Discriminating crop residues from soil by shortwave infrared reflectance, Agronomy Journal, vol. 93, pp. 125-131, 2001.

Epiphanio et al., Dependence of NDVI and SAVI on sun/sensor geometry and its effect on fAPAR relationships in alfalfa, Remote Sensing of Environment, vol. 51, pp. 351-360, 1995.

Erasmi et al., Determination of crop stress using spectral transformations of hyperspectral data, Proc. 3rd EARSeL Work, Imaging Spectroscopy, vol. 49, pp. 496-503, 2003.

Fick et al., Statistical Models for Predicting Alfalfa Herbage Quality from morphological or weather data, Journal of Production Agriculture, vol. 1, pp. 160-166, 1988.

Franzen et al., Algorithms for in-season nutrient management in cereals, Agronomy Journal, vol. 108, No. 5, pp. 1775-1781, 2016.

Fricke et al., Combining ultrasonic sward height and spectral signatures to assess the biomass of legume-grass swards, Computers and Electronics in Agriculture, vol. 99, pp. 236-247, 2013.

Gitelson et al., Signature analysis of leaf reflectance spectra: Algorithm development for remote sensing of chlorophyll, Journal of Plant Physiology, vol. 148pp. 494-500, 1996.

Grimsbo Jewett et al., Field sampling strategies for studies of alfalfa forage quality, Canadian Journal of Plant Science., vol. 81, pp. 703-712, 2001.

Hakl et al., The use of indirect methods for the prediction of lucerne quality in the first cut under the conditions of Central Europe, Czech Journal of Animal Science, vol. 55, No. 6, pp. 258-265, 2010.

Hintz et al., Prediction of alfalfa chemical composition from maturity and plant morphology, Crop Science, vol. 31, pp. 1561-1565, 1991.

Kalu et al., Quantifying morphological development of alfalfa for studies of herbage quality, Crop Science, vol. 21, pp. 267-271, 1981.

Kalu et al., 1983, Morphological stage of development as a predictor of alfalfa herbage quality, Crop Science, vol. 23, pp. 1167-1172.

Kendall et al., Intake and milk production of cows fed diets that differed in dietary neutral detergent fiber and neutral detergent fiber digestibility, Journal of Dairy Science, vol. 92, pp. 313-323, 2009.

Kratchunov et al., Estimation of lucerne forage quality by means of morphological and meteorological data, European Journal of Agronomy, vol. 4, No. 2, pp. 263-267, 1995.

Lamb et al., Five decades of alfalfa cultivar improvement: Impact on forage yield, persistence, and nutritive value, Crop Science, vol. 46, pp. 902-909, 2006.

Lyons et al., Estimating alfalfa yield from plant height, Crop, Forage and Turfgrass Management, 2. doi:10.2134/cftm2015.0203, 3 pages, 2016.

Mathews et al., Visualizing and quantifying vineyard canopy LAI using an unmanned aerial vehicle (UAV) collected high density structure from motion point cloud, Remote Sensing, vol. 5, pp. 2164-2183, 2013.

McRoberts et al., Application of local binary patterns in digital images to estimate botanical composition in mixed alfalfa-grass fields, Computers and. Electronics in Agriculture, vol. 123, pp. 95-103, 2016.

Mulla, Twenty five years of remote sensing in precision agriculture: Key advances and remaining knowledge gaps, Biosystems Engineering, vol. 114, pp. 358-371, 2013.

Oba et al., Evaluation of the importance of the digestibility of neutral detergent fiber from forage: Effects on dry matter intake and milk yield of dairy cows, Journal of Dairy Science, vol. 82, pp. 589-596, 1999.

Ollinger, Sources of variability in canopy reflectance and the convergent properties of plants, New Phytologist, vol. 189, pp. 375-394, 2011.

Owens et al., A rapid method for predicting alfalfa quality in the field, Journal of Production Agriculture, vol. 8, No. 4, pp. 491-495, 1995.

Pittman et al., Estimation of biomass and canopy height in bermudagrass, alfalfa, and wheat using ultrasonic, laser, and spectral sensors, Sensors, vol. 15, pp. 2920-2943, 2015.

Radtke et al, An evaluation of overhead laser scanning to estimate herbage removals in pasture quadrats, Agricutral and Forest Meteorology, vol. 150, pp. 1523-1528, 2010.

Rouse et al., Monitoring vegetation systems in the Great Plains with ERTS, Third ERTS Symp., NASA SP-351, pp. 309-317, 1973.

Sanderson, Predictors of alfalfa forage quality—validation with field data, Crop Science, vol. 32, pp. 245-250, 1992.

Sanderson et al, Morphological development of alfalfa as a function of growing degree days, Journal of Production Agriculture, vol. 7, No. 2, pp. 181-182, 1994.

Satter et al., Nitrogen requirement and utilization in dairy cattle, Journal of Dairy Science, vol. 58, No. 8, pp. 1219-1237, 1975.

Serrano et al., Remote sensing of nitrogen and lignin in Mediterranean vegetation from AVIRIS data: decomposing biochemical from structural signals, Remote Sensing of Environment, vol. 81, pp. 355-364, 2002.

Sharratt et al., Base temperature for the application of the growing-degree-day model to field-grown alfalfa, Field Crops Research, vol. 21, pp. 95-102, 1989.

Smeal et al., Alfalfa yield as related to transpiration, growth stage and environment, Irrigation Science, vol. 12, pp. 79-86, 1991.

Starks et al., Development of canopy reflectance algorithms for real-time prediction of bermudagrass pasture biomass and nutritive values, Crop Science, vol. 46, pp. 927-934, 2006.

Starks et al., Canopy visible and near-infrared reflectance data to estimate alfalfa nutritive attributes before harvest, Crop Science, vol. 56, pp. 484-494, 2016.

Sulc et al., Update on predicting harvest time for alfalfa, 12 pages, 1999.

Undersander et al., 2010, Relative forage quality, Univ. of Wisconsin-Ext, Madison, Focus on Forage, 12:1-3, http://fyi.uwex.edu/forage/files/2014/01/RFQ-FOF.pdf (accessed Jun. 30, 2017).

USDA—Economic Research Service, 2016, Feed grains database, USDA-ERS, Washington, D.C., http://www.ers.usda.gov/data-products/feed-grains-database.aspx (accessed Mar. 27, 2017).

USDA—National Agricultural Statistics Service Cropland Data Layer, 2016, Published crop-specific data layer, USDA-NASS, Washington, D.C., http://nassgeodata.gmu.edu/cropscape/ (accessed May 30, 2017).

(56) References Cited

OTHER PUBLICATIONS

UW—Extension Team Forage, 2016, Hay market report, Univ. of Wisconsin-Ext., Madison, http://fyi.uwex.edu/forage/h-m-r/ (accessed Mar. 27, 2017).

Zhang et al., The application of small unmanned aerial vehicle systems for precision agriculture: a review, Precision Agricultural, vol. 13, pp. 693-712, 2012.

* cited by examiner

INTEGRATED REMOTE SENSING TOOLS FOR TIMELY PREDICTIONS OF CROP QUALITY AND YIELD

CROSS-REFERENCE TO RELATED APPLICATION

The present application is based on and claims the benefit of U.S. Provisional patent application Ser. No. 62/371,294, filed Aug. 5, 2016, the content of which is hereby incorporated by reference in its entirety.

BACKGROUND

Throughout the alfalfa production season, careful and informed harvest decisions increase the chances of meeting production goals. The growth of a stand, from one cut to the next, will always vary according to stand health as well as a range of environmental factors. Accurate in-field assessment of an alfalfa crop is critical to maximize profitability, in terms of both quality and yield. In the upper Midwest, where forage demands are driven by the dairy industry, the value of a crop is especially dependent on forage quality. Greater quality means greater milk/ton, which means greater profitability per ton of forage.

Physical measurements of alfalfa maturity and height are currently the most accurate and consistent indicators of quality. Destructive sampling enables the calculation of maturity indices such as mean stage by count (MSC) and mean stage by weight (MSW). The MSC or MSW values can then be interpreted as indicators of forage quality parameters, highlighting the common understanding that forage quality decreases with increasing alfalfa maturity.

The efficacy of physical measurements is limited by time and labor required for sampling, and by the area effectively represented. Furthermore, the usefulness of these maturity indices may change as alfalfa is harvested earlier for higher quality and as new, novel varieties of alfalfa are being developed with reduced lignin content (i.e. higher digestible fiber). The introduction of these lines will introduce new flexibility into alfalfa harvest management and limit the applications of traditional assessment tools. Although alfalfa maturity will still correlate with quality in these new lines, higher quality will be maintained with greater maturity. Therefore, equal quality can be achieved with higher yields, or higher quality can be achieved with equal (conventional) yields. Precise and intensive management will be critical to optimize the use of these resources and maximize profit margins.

SUMMARY

A method includes receiving outside temperatures for a plurality of days and calculating growing degree units based on the received temperatures. Intensities for a plurality of wavelengths of light measured over at least one portion of a field containing a crop are received and are used with the growing degree units to predict yield value and/or a quality value for the crop. The predicted yield value and/or quality value for the crop is then displayed.

In accordance with a further embodiment, a computing device has a memory and a processor. The processor executes instructions to perform steps that include receiving a respective weather value for each of a plurality of days and receiving intensity values for a plurality of wavebands of light detected over a field containing a crop. The weather values and the intensity values are used to determine a predicted yield for the crop.

In accordance with a still further embodiment, a method involves using an unmanned aerial vehicle having at least one light sensor to collect light intensity values for a plurality of wavelengths of light above a crop. Weather values for a plurality of days are received and are used with the collected intensity values to predict at least one of a quality value and a yield for the crop.

DETAILED DESCRIPTION

Embodiments described herein combine remotely sensed data in the form of spectral reflectance with crop environment data to predict the quality of a growing crop, such as the Relative Forage Quality (RFQ) of alfalfa in the field. In accordance with one embodiment, the crop environment data is cumulative growing degree units (GDUs) which are a function of daily high and low temperatures since the last harvest of the alfalfa. In addition, in accordance with some embodiments, a small set of wavebands of the spectral reflectance are used to predict the quality of the growing crop. By using a small set of wavebands, simpler and less expensive spectral sensors can be used, greatly reducing the cost of the system.

Figure 1:
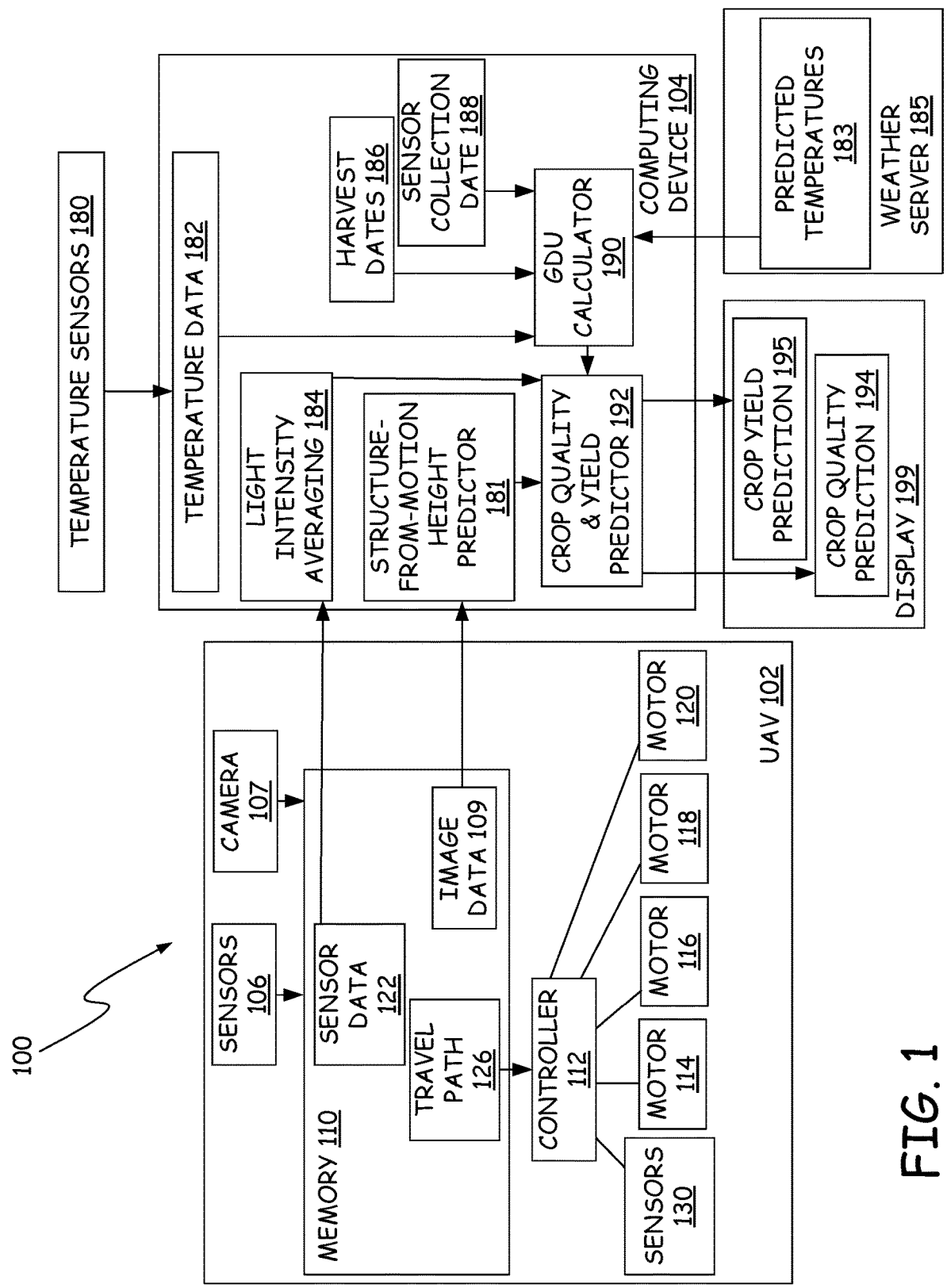
FIG. 1 is a block diagram of a system for predicting crop quality and yield in accordance with one embodiment.
Figure 2:
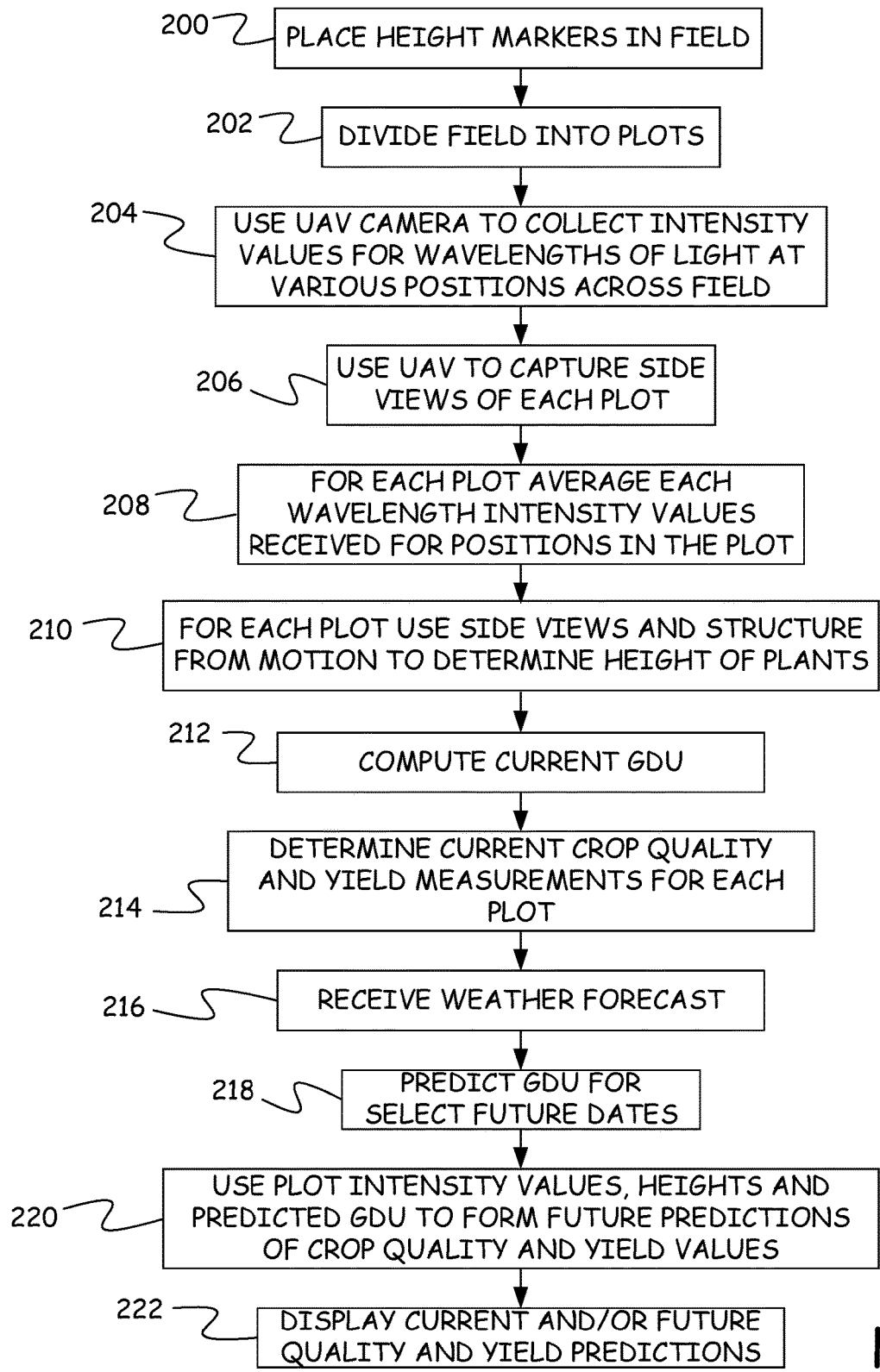
FIG. 2 is a flow diagram of a method of predicting crop quality in yield in accordance with one embodiment.

FIG. 1 provides a block diagram of a system 100 for predicting at least one of a quality and a yield of a growing crop in accordance with one embodiment. FIG. 2 provides a flow diagram of a method for predicting and displaying at least one of a quality of a growing crop and a yield of the growing crop.

System 100 includes UAV 102, computing device 104 and temperature sensors 180. UAV 102 includes sensors 106, camera 107, a memory 110, a controller 112 and motors, such as motors 114, 116, 118 and 120. Sensors 106 provide sensor data 122, which is stored in memory 110, and contains intensity values for various wavelengths of light. In accordance with some embodiments, each of sensors 106 is able to detect the intensity of a single respective wavelength of light. In other embodiments, some or all of sensors 106 detect the intensity of light across a band of wavelengths referred to as a waveband that is defined by the span of wavelengths in the band and the wavelength at the center of the band. Camera 107 captures images that are stored as image data 109. A travel path 126 is stored in memory 110 and represents the path that UAV 102 is to travel to capture spectral reflectance of a growing crop over a geographical area and positions for capturing images of the crop. Travel path 126 is provided to controller 112, which controls motors 114, 116, 118 and 120 to drive propellers so that UAV 102 follows travel path 126. One or more sensors, such as sensors 130 provide feedback to controller 112 as to the current position of UAV 102 and/or the accelerations that UAV 102 is experiencing. This feedback is used by controller 112 determine the location of UAV 102 along travel path 126.

The method of FIG. 2 begins at step 200 where height markers are placed in various locations in a field. At step 202, the field is optionally divided into sub-areas or plots to allow for more refined predictions of crop quality and yield.

At step 204, UAV 102 is flown over the field along travel paths 126 while light sensors 206 capture the intensity of a plurality of wavelengths and/or wavebands of light at a plurality of locations over the field. In accordance with one embodiment, sensor data is collected at multiple locations within each plot in the field. In accordance with other embodiments, a satellite is used in place of UAV 102 to capture the intensity of the plurality of wavelengths and/or wavebands of light at the plurality of locations over the field.

At step 206, UAV 102 is flown to select positions in travel paths 126 to capture images of the field that include a side view of the crop. At least some of the images include the height markers placed in the field at step 200. Note that steps 204 and 206 can be interwoven with each other such that UAV 102 switches back and forth between capturing light intensity values and capturing images of the field. In other embodiments, UAV 102 collects a continuous video along travel paths 126 in order to collect the images of the crop represented by step 206.

Periodically or in real-time, UAV 102 provides sensor data 122 and image data 109 to computing device 104. Sensor data 122 and image data 109 may be provided over a wireless connection, a wired connection, or a combination of both between UAV 102 and computing device 104.

At step 208, a light intensity averaging unit 184 in computing device 104 groups the light intensity values in sensor data 122 based on the plots where the intensity values were observed and forms average intensity values for each measured wavelength/waveband for each plot.

At step 210, a structure-from-motion height predictor 181 uses the side views of the plots to determine an average height of the plants in each plot. In accordance with one embodiment, structure-from-motion height predictor 181 uses multiple images of the plots to assign three-dimensional coordinates to the tops of plants in the plots and to height gradations on the height marker. The vertical coordinate of each plant top is then matched to a vertical coordinate of a height gradation on the height marker to retrieve the corresponding height. These heights are then averaged together across a plot to arrive at the average plant height of the plot.

Computing device 104 also receives temperature data 182 from temperature sensors 180. In accordance with one embodiment, temperature data 182 includes a high and a low temperature for each day of the growing season. Computing device 104 is also provided with harvest dates 186 and sensor collection dates 188. Harvest dates 186 are the dates when the crop was cut or planted and are used to set a start date for calculating a cumulative Growing Degree Units value. Sensor collection dates 188 are the dates that the spectral sensor data was collected. At step 212, temperature Data 182, harvest dates 186 and sensor collection dates 188 are provided to a Growing Degree Unit (GDU) calculator 190, which determines a cumulative number of Growing Degree Units between the latest sensor collection date and the immediately preceding harvest/planting date. In one embodiment, the cumulative GDU is calculated as:

$$GDU = \sum_{i=harvest\ day}^{sensor\ collection\ day} \left[ \frac{(\text{high } temp_i - \text{low } temp_i)}{2} - basetemp \right] \quad \text{EQ. 1}$$

where high $temp_i$ and low $temp_i$ are the high and low temperature for day i, basetemp is a base temperature for the crop, which for alfalfa is 5 degrees Celsius (41 degrees Fahrenheit) and the summation is taken over the days between the last harvest/planting and the sensor collection day.

In accordance with still further embodiments, the Growing Degree Units are alternatively computed using a base temperature that changes continuously from 3.5 degrees Celsius on April 1 to 10 degrees Celsius on July 31 and then remains at 10 degrees Celsius for the remainder of the growing season. Thus, the base temperature changes as a function of the date.

The cumulative GDU is provided to a crop quality & yield predictor 192 together with the average intensity values for selected wavebands of light from sensor data 122. In accordance with some embodiments, crop quality & yield predictor 192 also receives an average height for each plot from structure-from-motion height predictor 181.

At step 214, crop quality & yield predictor 192 predicts a crop quality value 194 and a yield value 195 for each plot. In accordance with one embodiment, the yield and crop quality values are calculate using a constant, the cumulative GDU (GDU) and the average intensity of light across seven wavebands as:

Yield or Crop Quality=$a+bGDU+cW1+dW2+eW3+fW4+gW5+hW6+iW7$ where a, b, c, d e, f, g, h, and i are constants, GDU is the cumulative GDU, and W1-W7 are the intensity values for seven different wavebands/wavelengths.

In accordance with one particular embodiment, seven common wavebands were identified as a "utility set" for predictions of alfalfa yield, and the following crop qualities: Crude Protein (CP), Neutral Detergent Fiber (NDF), and Neutral Detergent Fiber digestibility (NDFd). In this example, all wavebands (W1, W2, etc.) used are the average reflectance values of a 20 nm waveband, centered on a specified wavelength. For example, R551 would be the average reflectance value within the spectral range of 541 to 561 nm. The utility spectra identified from this work are: W1=R351, W2=R398, W3=R4361, W4=R551, W5=R667, W6=R712, W7=R1077. These values are used in combination with environmental data (cumulative GDUs since cut) to make predictions of yield (kg DM ha-1), CP (%), NDF (%), and NDFd (%) as follows:

YIELD (kg $ha$-1)=905.30+3.79(GDU)+50707.95 (W1)−404246.8(W2)−99386.31(W3)+41741.32 (W4)+324481.6(W5)−65578.65(W6)+16581.55 (W7)

CP (%)=29.56−0.02801(GDU)−231.79(W1)+831.55 (W2)−142.52(W3)+198.57(W4)+42.86(W5)− 117.61(W6)+0.74(W7)

NDF (%)=27.31+0.04662(GDU)−370.94(W1)− 1057.99(W2)+804.80(W3)−327.14(W4)−104.35 (W5)+146.93(W6)−3.39(W7)

NDFd (%)=41.50−0.04065(GDU)−2266.00(W1)+ 4908.21(W2)−513.76(W3)+362.07(W4)−495.86 (W5)−242.37(W6)+7.19(W7)

In accordance with one embodiment, the GDU values used in the equations above are determined using a base temperature that changes as a function of the date.

Figure 3:
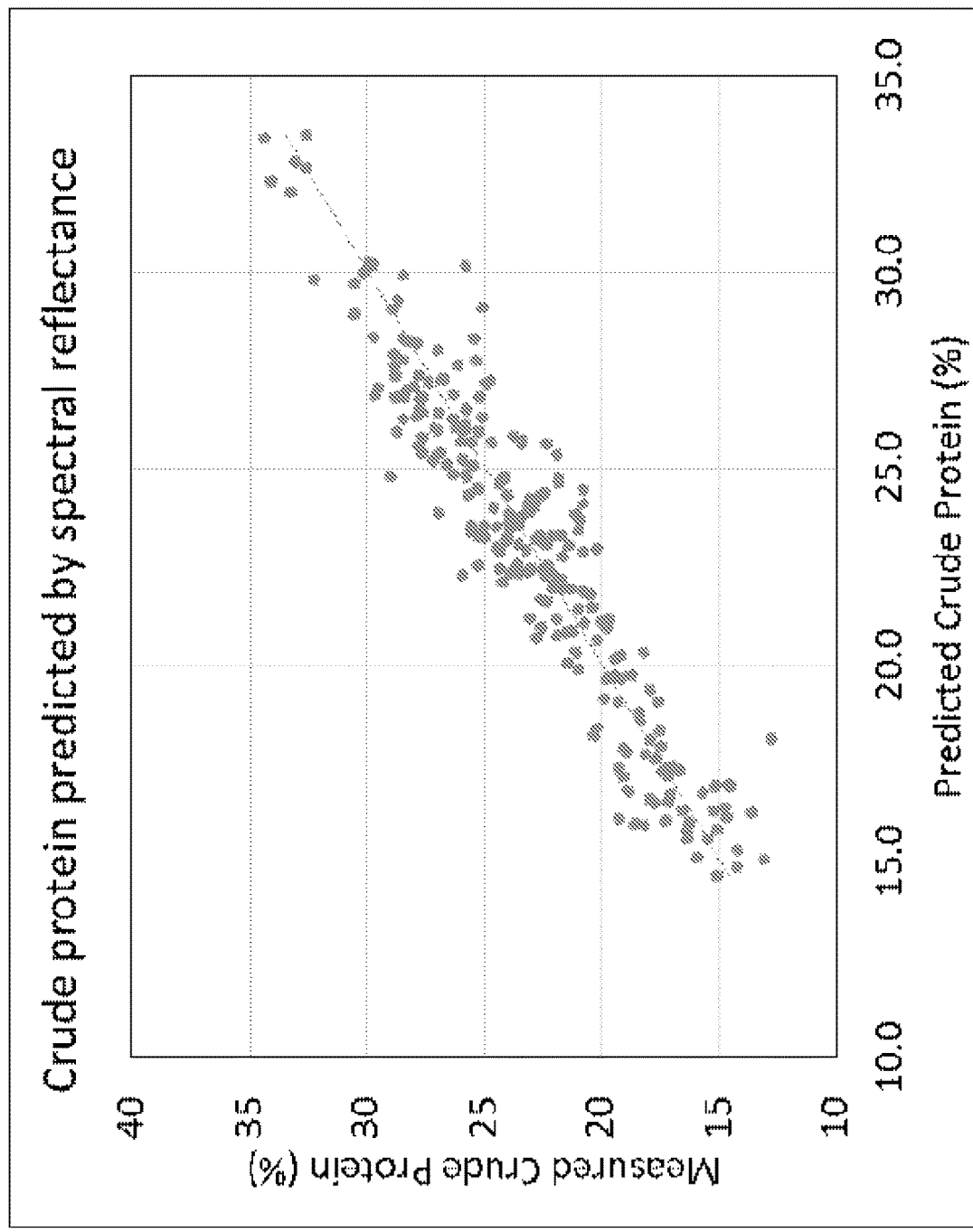
FIG. 3 is a graph showing predicted versus actual Relative Forage Quality.

FIG. 3 provides a graph of the relationship between Crude Protein values predicted through the equation above and measured Crude Protein values.

In other embodiments, the canopy height (height) determined by structure-from-motion height predictor 181 is used with the waveband intensity values and the GDU values to improve the model fit as:

YIELD (kg ha-1)=519.23+5.53(GDU)−3.02(height)−
43139.7($W1$)−161156.8($W2$)−98110.2($W3$)+
58762.78($W4$)+282037.9($W5$)−88519.13($W6$)+
18318.6($W7$)

CP (%)=32.24−0.02876(GDU)−0.03948(height)+
187.94($W1$)+92.42($W2$)+41.62($W3$)+232.17
($W4$)−42.69($W5$)−126.19($W6$)+2.06($W7$)

NDF (%)=19.90+0.05015(GDU)+0.0809(height)−
935.07($W1$)−5.74($W2$)−130.72($W3$)−417.97
($W4$)+331.92($W5$)+254.01($W6$)−10.61($W7$)

NDFd (%)=58.45−0.06150(GDU)−0.09573(height)−
764.08($W1$)+1061.77($W2$)+144.11($W3$)+383.53
($W4$)−340.05($W5$)−189.04($W6$)+10.67($W7$)

In accordance with one embodiment, the GDU values used in the equations above are determined using a base temperature that changes as a function of the date.

These equations could be re-fit using a lower number of wavebands, or a wider or narrower spectral resolution, depending on technical restrictions or affordability of the technology. Fewer wavebands at lower resolution (wider bands) generally equates to a lower cost sensor. The equations presented above were selected for optimum statistical predictive power.

As the equations presented have been calibrated across a range of alfalfa yield and nutritive value, the same approach could be used to develop tools for other crop species and assessments. These could include estimations of pest or disease pressure, nutrient deficiencies, or drought stress. Equations would be developed from spectral measurements across a range of the given response variable. One example would be to apply a range of fertilizer treatments (varying levels for a given nutrient) under nutrient-limiting conditions to identify associated spectral properties and most relevant wavebands to detect deficiency.

Although cumulative Growing Degree Units are used in the embodiments above as the crop environment data for predicting the crop quality, in other embodiments, other crop environment data is used. For example, in other embodiments one or more of rainfall, relative humidity, wind speeds, field history, stand age, plant density, fertility and soil type are used with or in place of GDU.

The yield values and crop quality values are computed for each date that light intensity values are collected. This creates a set of yield values and crop quality values across a range of dates.

At step 216, GDU calculator 190 receives a weather forecast that includes predicted high and low temperatures 183 for future dates from a weather server 185. At step 218, GDU calculator 190 predicts future GDU values using a combination of past temperature data 182 and predicted temperature data 183. In particular, GDU calculator 190 performs the summation of equation 1 from the last harvest/planting date to some chosen future date using the actual measured temperatures for past and current dates and the predicted temperatures for future dates. During step 218, GDU calculator 190 can use a fixed base temperature or a base temperature that changes as a function of the date.

At step 220, the light intensity averages for the plots, the predicted future GDU values, and optionally the plant heights, are used to compute crop quality and yield values for each of the plots.

Figure 4:
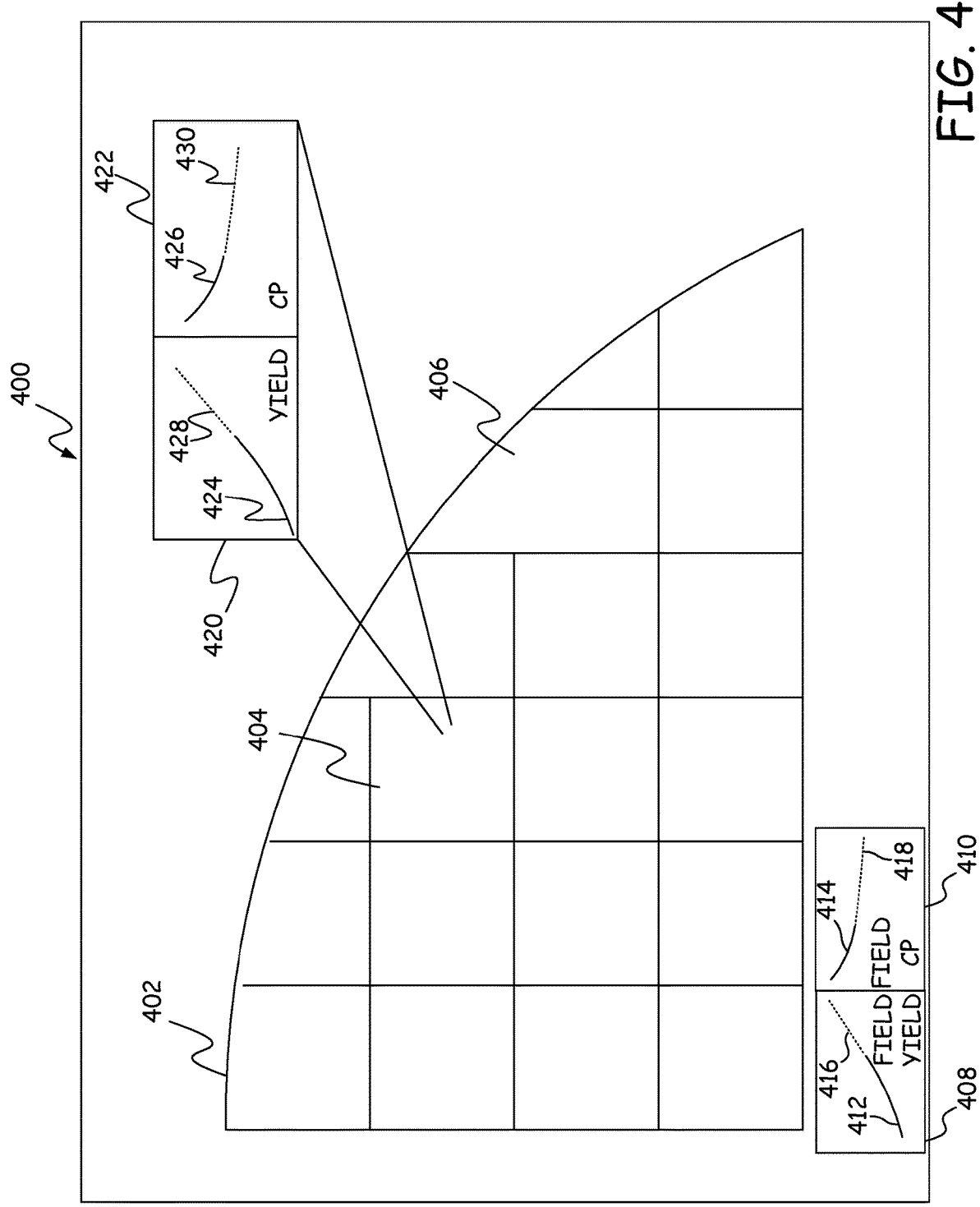
FIG. 4 is an example of a user interface showing crop quality and yield values for plots in a field.

At step 222, the crop quality and yield values for the plots are displayed in a user interface on display 199. FIG. 4 provides an example user interface 400 showing a plan view of a field 402 divided into plots such as plots 404 and 406, for example. FIG. 4 includes a field yield graph 408 and a field crop quality graph 410 that provide graphs of average yield and crop quality across the field for past, present, and future dates. In particular, solid lines 412 and 414 show past average yield predictions and average crop quality predictions, respectively, with the present day's predictions shown at the end of the solid lines and dotted lines 416 and 418 show future average yield predictions and average crop quality predictions, respectively. In addition, by hovering over a plot on the map of the field, a pop-up window is displayed showing graphs of one or more crop qualities and a crop yield for that particular plot. For example, in FIG. 4, a plot yield graph 420 and a crop quality graph 422 are shown for plot 404. In graphs 420 and 422, solid lines 424 and 426 represent past yield and crop quality values, respectively, with the end of the solid lines represent the current days values and dotted lines 428 and 430 represent further yield and crop quality values, respectively.

An example of a computing device 10 that can be used as a server and/or client device in the various embodiments is shown in the block diagram of FIG. 4. For example, computing device 10 may be used to perform any of the steps described above. Computing device 10 of FIG. 4 includes a processing unit (processor) 12, a system memory 14 and a system bus 16 that couples the system memory 14 to the processing unit 12. System memory 14 includes read only memory (ROM) 18 and random access memory (RAM) 20. A basic input/output system 22 (BIOS), containing the basic routines that help to transfer information between elements within the computing device 10, is stored in ROM 18.

Embodiments of the present invention can be applied in the context of computer systems other than computing device 10. Other appropriate computer systems include handheld devices, multi-processor systems, various consumer electronic devices, mainframe computers, and the like. Those skilled in the art will also appreciate that embodiments can also be applied within computer systems wherein tasks are performed by remote processing devices that are linked through a communications network (e.g., communication utilizing Internet or web-based software systems). For example, program modules may be located in either local or remote memory storage devices or simultaneously in both local and remote memory storage devices. Similarly, any storage of data associated with embodiments of the present invention may be accomplished utilizing either local or remote storage devices, or simultaneously utilizing both local and remote storage devices.

Computing device 10 further includes a hard disc drive 24, a solid state memory 25, an external memory device 28, and an optical disc drive 30. External memory device 28 can include an external disc drive or solid state memory that may be attached to computing device 10 through an interface such as Universal Serial Bus interface 34, which is connected to system bus 16. Optical disc drive 30 can illustratively be utilized for reading data from (or writing data to) optical media, such as a CD-ROM disc 32. Hard disc drive 24 and optical disc drive 30 are connected to the system bus 16 by a hard disc drive interface 32 and an optical disc drive interface 36, respectively. The drives, solid state memory and external memory devices and their associated computer-readable media provide nonvolatile storage media for computing device 10 on which computer-executable instructions and computer-readable data structures may be stored. Other types of media that are readable by a computer may also be used in the exemplary operation environment.

A number of program modules may be stored in the drives, solid state memory 25 and RAM 20, including an operating system 38, one or more application programs 40, other program modules 42 and program data 44. For example, application programs 40 can include instructions for performing any of the steps described above. Program data can include any data used in the steps described above.

Input devices including a keyboard 63 and a mouse 65 are connected to system bus 16 through an Input/Output interface 46 that is coupled to system bus 16. Monitor 48 is connected to the system bus 16 through a video adapter 50 and provides graphical images to users. Other peripheral output devices (e.g., speakers or printers) could also be included but have not been illustrated. In accordance with some embodiments, monitor 48 comprises a touch screen that both displays input and provides locations on the screen where the user is contacting the screen.

Computing device 10 may operate in a network environment utilizing connections to one or more remote computers, such as a remote computer 52. The remote computer 52 may be a server, a router, a peer device, or other common network node. Remote computer 52 may include many or all of the features and elements described in relation to computing device 10, although only a memory storage device 54 has been illustrated in FIG. 5. The network connections depicted in FIG. 5 include a local area network (LAN) 56 and a wide area network (WAN) 58. Such network environments are commonplace in the art.

Computing device 10 is connected to the LAN 56 through a network interface 60. Computing device 10 is also connected to WAN 58 and includes a modem 62 for establishing communications over the WAN 58. The modem 62, which may be internal or external, is connected to the system bus 16 via the I/O interface 46.

Figure 5:
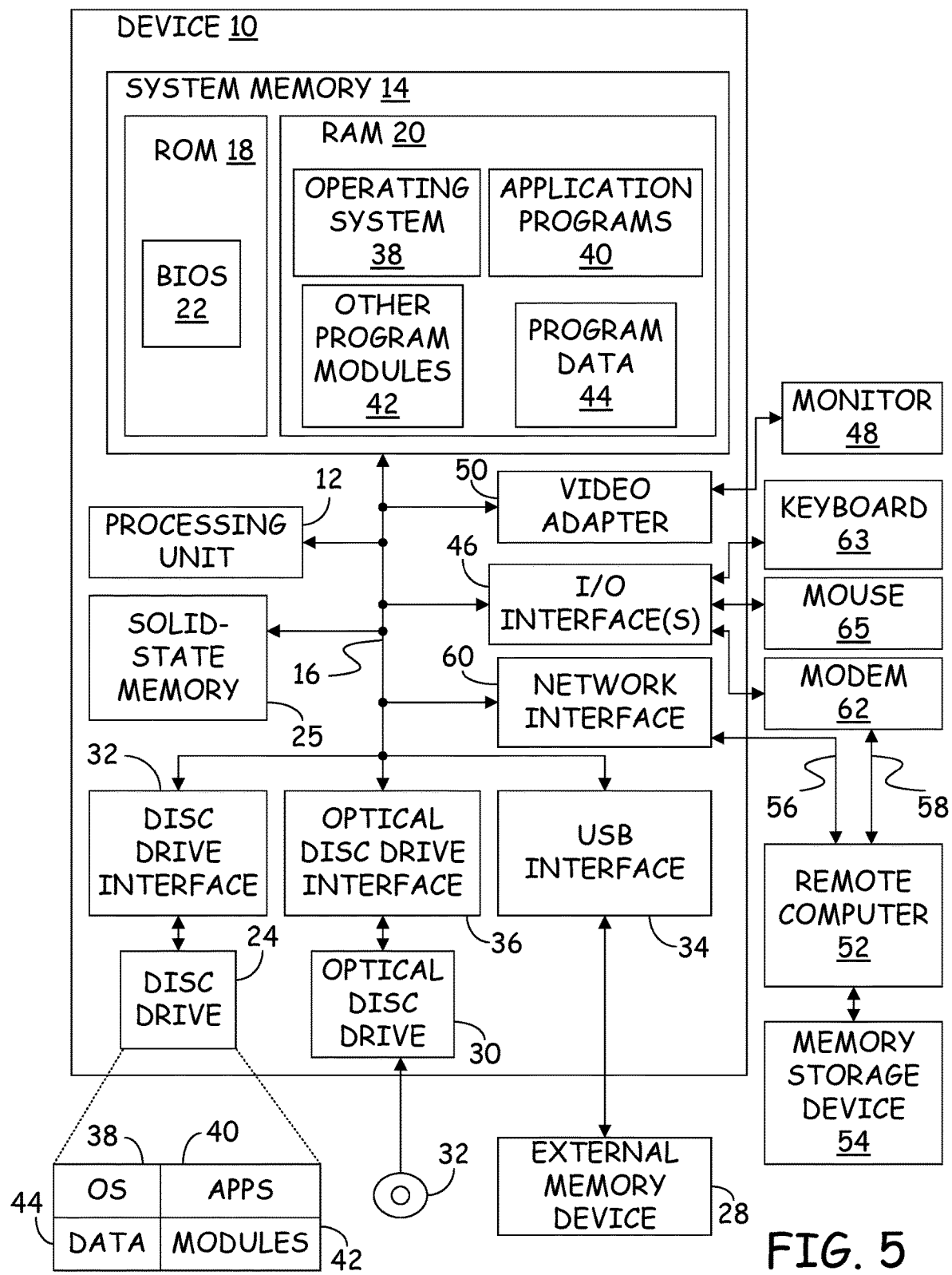
FIG. 5 is a block diagram of a computing device that can be used as a server or client device in the various embodiments.

In a networked environment, program modules depicted relative to computing device 10, or portions thereof, may be stored in the remote memory storage device 54. For example, application programs may be stored utilizing memory storage device 54. In addition, data associated with an application program may illustratively be stored within memory storage device 54. It will be appreciated that the network connections shown in FIG. 5 are exemplary and other means for establishing a communications link between the computers, such as a wireless interface communications link, may be used.

Although the present invention has been described with reference to preferred embodiments, workers skilled in the art will recognize that changes may be made in form and detail without departing from the spirit and scope of the invention.

What is claimed is:

1. A method comprising:
    an unmanned aerial vehicle interweaving capturing light intensity values of a portion of a field containing a crop and capturing images of the field;
    receiving outside temperatures for a plurality of days;
    determining growing degree units based on the received temperatures;
    determining a height for the crop using structure-from-motion and the captured images of the field;
    using the intensities in combination with the height and the growing degree units to predict a quality value for the crop; and
    displaying the predicted quality value for the crop.

2. The method of claim 1 further comprising using the intensities in combination with the growing degree units to predict a yield for the crop and displaying the yield for the crop.

3. The method of claim 1 wherein receiving outside temperatures for a plurality of days comprises receiving a maximum temperature for each day since a last harvest of the crop.

4. The method of claim 3 wherein receiving outside temperatures further comprises receiving a predicted maximum temperature for at least one day in the future.

5. The method of claim 1 wherein using the intensities for the plurality of wavelengths comprises grouping at least some of the wavelengths into a waveband and averaging intensities of wavelengths in the waveband to form an intensity for the waveband.

6. A system comprising:
    an unmanned aerial vehicle interweaving capturing light intensity values of a portion of a field containing a crop and capturing images of the field;
    a computing device comprising:
        a memory containing instructions; and
        a processor executing the instructions in the memory to perform steps comprising:
            receiving a respective weather value for each of a plurality of days;
            receiving the intensity values for the plurality of wavebands of light detected over the field containing the crop;
            determining a height of the crop using structure from motion and the captured images of the field; and
            using the weather values in combination with the height and the intensity values to determine a predicted yield for the crop.

7. The computing device of claim 6 wherein receiving a weather value comprises receiving a combination of past weather values and future weather values.

8. The computing device of claim 7 wherein receiving a weather value comprises receiving a temperature for each of the plurality of days.

9. The computing device of claim 8 wherein using the weather values to determine the predicted yield comprises choosing a date and using the received temperatures for all days between a last harvest date and the chosen date to determine growing degree units between the two dates and using the growing degree units to determine the predicted yield on the chosen date.

10. The computing device of claim 9 wherein the chosen date is a future date.

11. The computing device of claim 6 further comprising using the weather values and the intensity values to determine a predicted quality measure for the crop.

12. A method comprising:
    using an unmanned aerial vehicle having at least one light sensor to interweave between collecting light intensity values for a plurality of wavelengths of light above a crop and capturing pictures of the crop;
    receiving weather values for a plurality of days;
    using the pictures of the crop to estimate a height of the crop;

using the collected intensity values in combination with the estimated height of the crop and the weather values to predict a quality value for the crop displaying the quality value on an electronic display.

13. The method of claim 12 wherein using the weather values to predict the quality value for the crop comprises using the weather values to determine growing degree units since a last harvest of the crop.

14. The method of claim 13 wherein determining a growing degree unit for a date comprises using a base temperature that is a function of the date.

15. The method of claim 12 wherein receiving the weather values for a plurality of days comprises receiving whether values measured for past days and predicted weather values predicted for future days.

16. The method of claim 12 wherein using the collected intensity values to predict the quality value for the crop comprises averaging intensity values for wavelengths in a waveband to form an average intensity for the waveband and using the average intensity for the waveband to predict the quality value for the crop.

* * * * *